(12) United States Patent
Kadobayashi et al.

(10) Patent No.: US 8,690,573 B2
(45) Date of Patent: Apr. 8, 2014

(54) METHOD OF ARRANGING ARTIFICIAL TEETH

(71) Applicant: Kabushiki Kaisha Shofu, Kyoto (JP)

(72) Inventors: Yusei Kadobayashi, Kyoto (JP); Toshihide Fujii, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 13/961,260

(22) Filed: Aug. 7, 2013

(65) Prior Publication Data

US 2013/0323682 A1 Dec. 5, 2013

Related U.S. Application Data

(63) Continuation of application No. 12/638,061, filed on Dec. 15, 2009, now abandoned.

(30) Foreign Application Priority Data

Dec. 16, 2008 (JP) ................................. 2008-319123
Oct. 2, 2009 (JP) ................................. 2009-230660

(51) Int. Cl.
*A61C 13/10* (2006.01)

(52) U.S. Cl.
USPC .......................................................... 433/196

(58) Field of Classification Search
USPC ....................... 433/25, 53, 167, 171, 196, 215
See application file for complete search history.

(56) References Cited

U.S. PATENT DOCUMENTS

| | | | |
|---|---|---|---|
| 1,657,673 A | 1/1928 | Gysi | |
| 1,696,422 A | 12/1928 | Thayer | |
| 1,713,267 A | 5/1929 | Crowley | |
| 1,822,837 A | 9/1931 | Avery et al. | |
| 2,144,198 A | 1/1939 | Page | |
| 2,169,719 A | 8/1939 | Bush | |
| 2,203,226 A | 6/1940 | Rudolf | |
| 2,419,248 A | 4/1947 | Blanchard | |
| 2,570,562 A | 10/1951 | Kinsley | |
| RE24,045 E | 7/1955 | Dahl | |
| 3,252,220 A | 5/1966 | Goddard | |
| 3,306,632 A | 2/1967 | Stahmer | |

(Continued)

FOREIGN PATENT DOCUMENTS

| | | |
|---|---|---|
| JP | 2-37611 | 3/1990 |
| JP | 11-290347 | 10/1999 |
| JP | 2002-177301 | 6/2002 |

OTHER PUBLICATIONS

Notification of Reason for Refusal issued Feb. 4, 2013 in corresponding Japanese Application No. 2009-230660.

*Primary Examiner* — Hao D Mai

(74) *Attorney, Agent, or Firm* — Wenderoth, Lind & Ponack, L.L.P.

(57) ABSTRACT

Artificial teeth arranged in plates attachable in an oral cavity as a dental prosthetic appliance, in which arrangement direction indication parts showing a directivity of arrangement in the plates extending in an apical-cervical direction or in a mesiodistal direction are provided at a vestibular side or an oral side. The arrangement direction indication parts extending in the apical-cervical direction are positioned linearly as seen from the vestibular side in an occluded state of mandibular teeth and maxillary teeth. The arrangement direction indication parts extending in the mesiodistal direction are positioned linearly as seen from the vestibular side in the state in which the teeth are arranged in the plates. The artificial teeth are arranged at an appropriate position according to an oral environment of each patient, without requiring advanced skill and experience.

4 Claims, 10 Drawing Sheets

(56) References Cited

U.S. PATENT DOCUMENTS

| | | |
|---|---|---|
| 3,644,995 A | 2/1972 | Olsson |
| 3,755,898 A | 9/1973 | Warren |
| 3,878,611 A | 4/1975 | Seaman |
| 3,925,896 A | 12/1975 | McDowell |
| 4,047,303 A | 9/1977 | Ziofsky et al. |
| 4,194,288 A | 3/1980 | Hass |
| 4,302,884 A | 12/1981 | Pallone |
| 4,642,050 A | 2/1987 | Heinix |
| 4,747,776 A | 5/1988 | Sudderth |
| 4,797,096 A | 1/1989 | Ito et al. |
| 4,906,186 A | 3/1990 | France, Jr. |
| 5,049,075 A | 9/1991 | Barrut |
| 5,083,920 A | 1/1992 | Molteni et al. |
| 5,363,561 A | 11/1994 | Essary |
| 5,680,857 A | 10/1997 | Pelikan |
| 5,951,289 A | 9/1999 | Kura et al. |
| 7,267,549 B2 | 9/2007 | Monkmeyer |
| 2004/0110110 A1 | 6/2004 | Chishti et al. |
| 2004/0137407 A1 | 7/2004 | Lauciello |
| 2006/0141420 A1 | 6/2006 | Schwartz et al. |

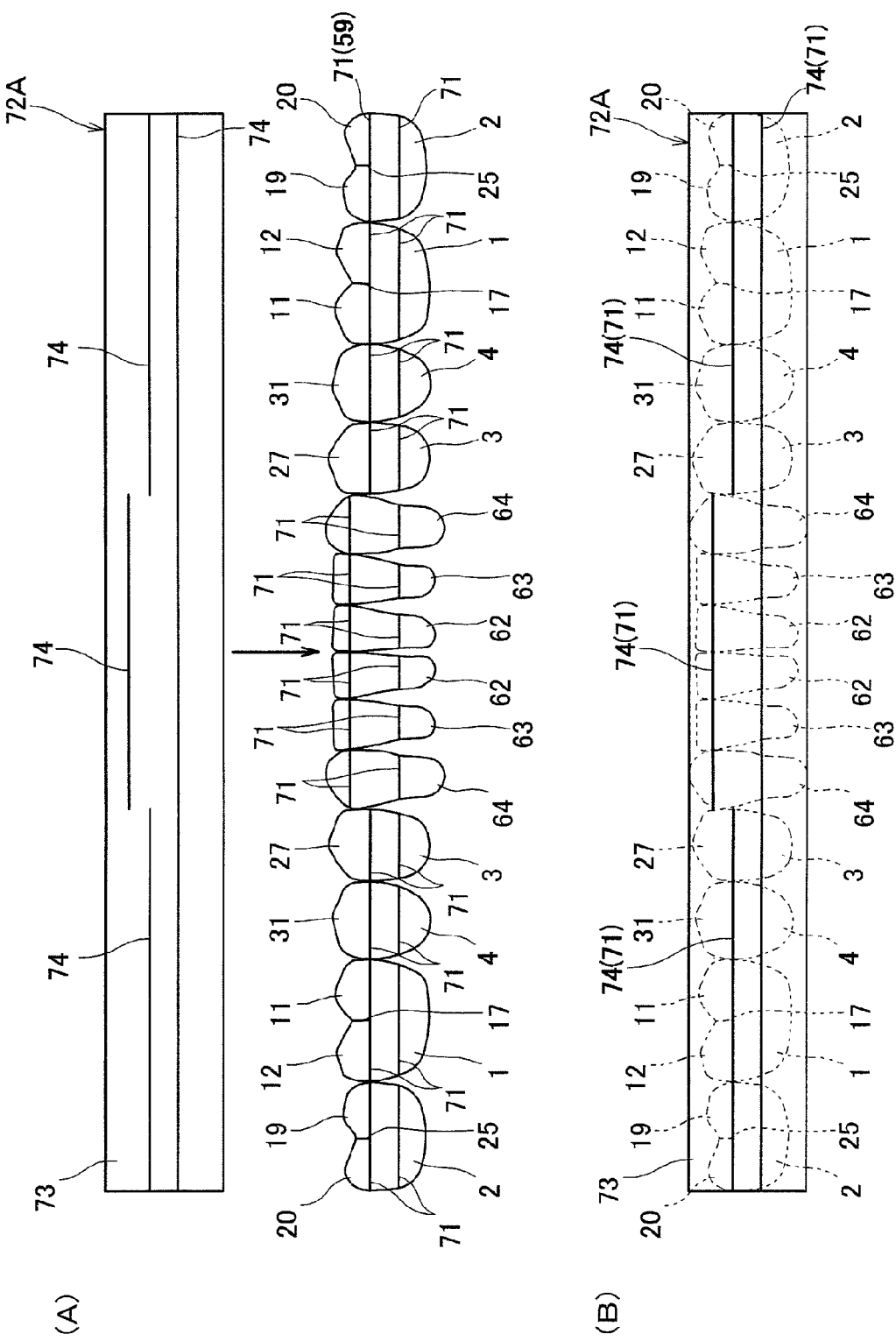

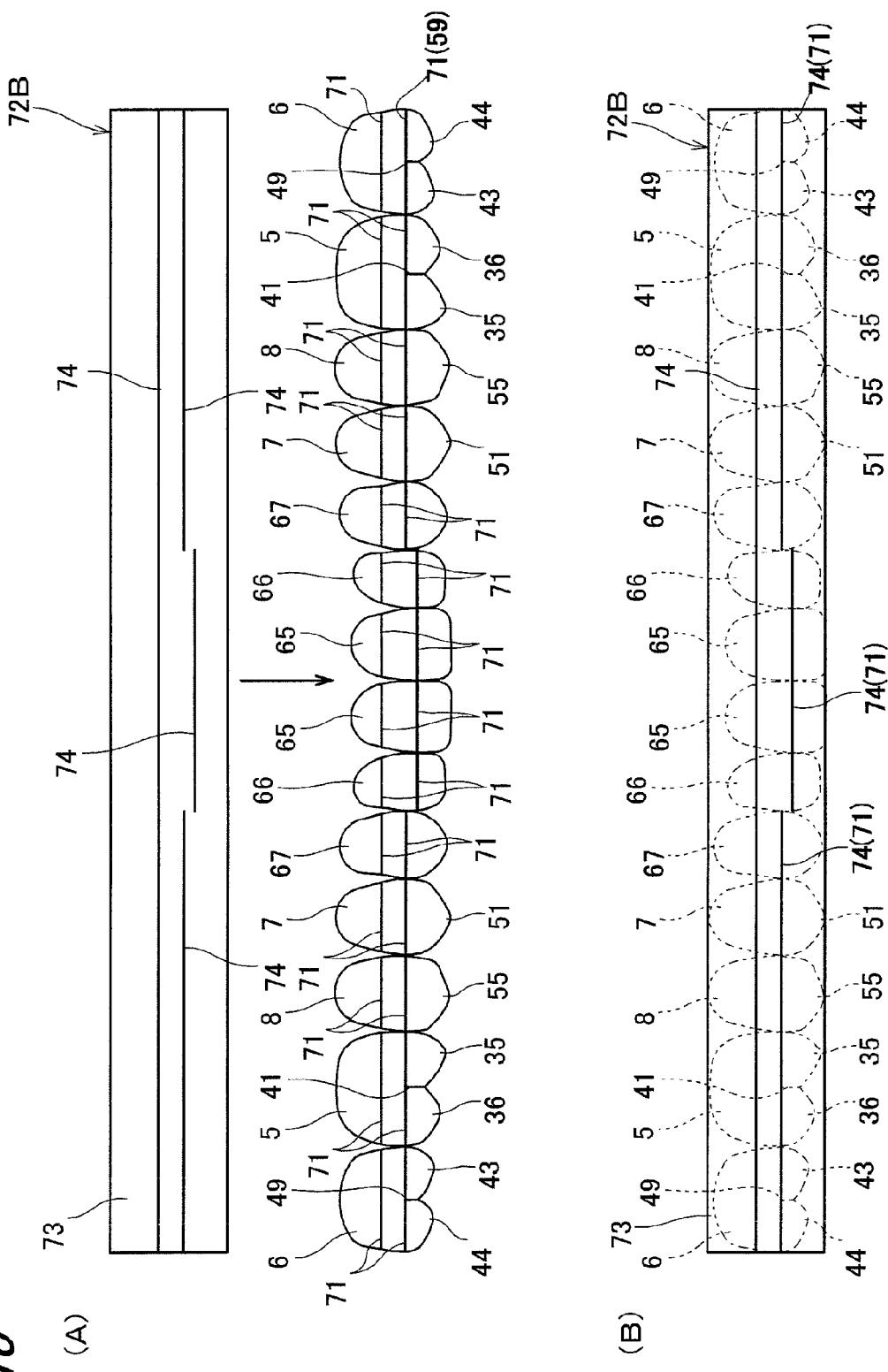

METHOD OF ARRANGING ARTIFICIAL TEETH

BACKGROUND OF THE INVENTION

1. Field of the Invention

The present invention relates to artificial teeth which can be arranged easily when making a dental prosthetic appliance and are easy in mastication when wearing it as dentures.

2. Description of the Related Art

Arrangement of artificial molar teeth when making a dental prosthetic appliance required advanced skill and experience. In particular, it was difficult to arrange the adjacent teeth in an appropriate positional relation. Specifically, in dentures, the artificial teeth to be arranged in six degrees of freedom (position and angle) must be arranged at specified positions, and the dentures must be made for individual patients. It was, however, extremely difficult to arrange the teeth in specified positions on the upper and lower jaws, or arrange the adjacent teeth in specified positions. In conventional artificial teeth, accordingly, in order to obtain an ideal mastication, it was necessary to do a large amount of grinding after the arrangement, or change a surface condition largely.

JP-A-2002-177301 discloses artificial molar teeth in which a lingual cusp, a buccal cusp, and a fossa are formed on the occlusal surface of upper molar teeth, and a lingual cusp, a buccal cusp, and a fossa are formed on the occlusal surface of lower antagonist molar teeth. In these artificial molar teeth, at the central occlusal position, the upper molar teeth and the lower antagonist molar teeth are configured so that the lingual cusp of the upper molar teeth may occlude and contact with the fossa of the lower antagonist molar teeth, and that the buccal cusp of the lower antagonist molar teeth may occlude and contact with the fossa of the upper molar teeth.

In the artificial molar teeth of JP-A-2002-177301, when making the dentures, it is easy to arrange in the wax alveolar ridge and adjust the occlusion by grinding or the like. Also when using the dentures, the dentures are stable without being inverted. In the masticatory efficiency including grinding, chewing, and cutting of food, an occlusion close to a full balanced occlusion is obtained. It is also easy to change to a lingualized occlusion not only when making the dentures but also when correcting the dentures.

However, in the artificial molar teeth of JP-A-2002-177301, since the positions of the cusp and the fossa of antagonist molar teeth are limited, and it is hard to identify the positions of the cusp and the fossa at the time of arrangement, the artificial teeth cannot be easily arranged in normal arrangement positions. As a result, a normal mastication may not be obtained, and adjustment by grinding or the like after arrangement may be needed.

SUMMARY OF THE INVENTION

It is an object of the present invention to provide artificial molar teeth that can be adjusted at appropriate positions according to the oral cavity environment of each patient, without requiring advanced skills and experiences.

To achieve the above object, first artificial teeth of the present invention are configured such that artificial teeth arranged in plates attached in an oral cavity as a dental prosthetic appliance, wherein arrangement direction indication parts showing a directivity of arrangement in the plates extending in an apical-cervical direction are provided at a vestibular side or an oral side.

These artificial teeth are artificial teeth arranged in plates attached in an oral cavity as a dental prosthetic appliance, having two or more teeth to be adjacently arranged in a mesiodistal direction, wherein arrangement direction indication parts showing a directivity of arrangement in the plates extending in an apical-cervical direction are provided at a vestibular side or an oral side of the teeth, and the arrangement direction indication parts of the teeth are extended generally in parallel in the state arranged in the plates.

Alternatively, these artificial teeth are artificial teeth having maxillary teeth and mandibular teeth arranged in plates attached in an upper jaw and a lower jaw in an oral cavity as a dental prosthetic appliance, wherein arrangement direction indication parts showing a directivity of arrangement in the plates extending in an apical-cervical direction are provided at a vestibular side or an oral side of the maxillary teeth and the mandibular teeth, and the arrangement direction indication parts of the maxillary teeth and the mandibular teeth are positioned generally in parallel in the state arranged in the plates.

In a completed state, the plate of the dentures is made of resin. This resin-made plate is formed in place of wax rim of a temporary plate after arrangement of artificial teeth. In the specification herein, therefore, "when arranging on the plate" means specifically "when arranging on the wax rim of the temporary plate."

Since the first artificial teeth have arrangement direction indication parts extending in the apical-cervical direction, when the teeth are arranged adjacently in a mesiodistal direction, the teeth can be arranged in a specified direction only by arranging so that each arrangement direction indication part may be extended in parallel. Similarly, when arranging the maxillary teeth and mandibular teeth up and down, only by arranging so that each arrangement direction indication part may be positioned in parallel, the teeth can be arranged in a specified direction. Therefore, the teeth may be adjusted and arranged in specified positions without requiring advanced skills and experiences.

These artificial teeth are preferably configured such that a cervical side end portion of the arrangement direction indication parts is positioned on a maximum contour ridge line generally in parallel to the mesiodistal direction in the state arranged in the plates. Thus, when arranging adjacent teeth, the position in the apical-cervical direction can be adjusted easily without requiring advanced skills and experiences.

In view of arranging the teeth adjacently in the mesiodistal direction, the cervical side end portion of the arrangement direction indication parts and a contact point of adjacent teeth in the state arranged in the plates are preferably positioned on a flat plane generally parallel to the mesiodistal direction. Thus, similarly to the above, when arranging the adjacent teeth, the position in the apical-cervical direction can be adjusted easily without requiring advanced skills and experiences.

In view of arranging the teeth up and down, the arrangement direction indication parts of the maxillary teeth and the mandibular teeth are preferably positioned linearly as seen from the vestibular side at a central occlusion position. Thus, when arranging the upper and lower occlusal teeth, the position in the mesiodistal direction can be adjusted easily without requiring advanced skills and experiences.

The arrangement direction indication parts of these artificial teeth are lateral grooves extending from an apical side toward a cervical direction in the state arranged in the plates.

The arrangement direction indication parts are ridge lines formed by facets formed at a mesial side and a distal side of a protruding cusp.

The arrangement direction indication parts are lines formed to extend from the apical side toward the cervical direction in the state arranged in the plates, by coloring of the vestibular side and the oral side.

The second artificial teeth of the present invention are configured such that artificial teeth arranged in plates attached in an oral cavity as a dental prosthetic appliance, wherein arrangement direction indication parts showing a directivity of arrangement in the plates extending in a mesiodistal direction are provided at a vestibular side or an oral side.

These artificial teeth are artificial teeth arranged in plates attached in an oral cavity as a dental prosthetic appliance, having two or more teeth to be adjacently arranged in a mesiodistal direction, wherein arrangement direction indication parts showing a directivity of arrangement in the plates extending in the mesiodistal direction are provided at a vestibular side or an oral side of the teeth, and the arrangement direction indication parts of the teeth are positioned generally in parallel in the state arranged in the plates.

Alternatively, these artificial teeth are artificial teeth having maxillary teeth and the mandibular teeth arranged in plates attached in an upper jaw and a lower jaw in an oral cavity as a dental prosthetic appliance, wherein arrangement direction indication parts showing a directivity of arrangement in the plates extending in a mesiodistal direction are provided at a vestibular side or an oral side of the maxillary teeth and the mandibular teeth, and the arrangement direction indication parts of the maxillary teeth and the mandibular teeth are extended generally in parallel in the state arranged in the plates.

Since the second artificial teeth have arrangement direction indication parts extending in the mesiodistal direction, when the teeth are arranged adjacently in the mesiodistal direction, the teeth can be arrange in a specified direction only by arranging so that each arrangement direction indication part may be positioned in parallel. Similarly, when arranging the maxillary teeth and mandibular teeth up and down, only by arranging so that each arrangement direction indication part may be extended in parallel, the teeth can be arranged in a specified direction. Therefore, the teeth may be adjusted and arranged in specified positions without requiring advanced skills and experiences.

These artificial teeth are preferably configured such that the arrangement direction indication parts are positioned on a maximum contour ridge line generally parallel to the mesiodistal direction in the state arranged in the plates. Thus, without requiring advanced skills and experiences, only by arranging the teeth so that each arrangement direction indication part may be continuous and linear, when arranging the adjacent teeth, the position in the apical-cervical direction can be adjusted easily.

In view of arranging the teeth adjacently in the mesiodistal direction, the arrangement direction indication parts are preferably positioned linearly as seen from the vestibular side in the state arranged in the plates. Thus, similarly to the above, when arranging the adjacent teeth, the position in the apical-cervical direction can be adjusted easily without requiring advanced skills and experiences.

As described above, in the artificial teeth having the arrangement direction indication parts showing the directivity of the arrangement in the plates extending in the apical-cervical direction or the mesiodistal direction, provided on the vestibular side or the oral side, as an arrangement confirmation sheet for confirming an arrangement state, it is preferred that confirm lines overlapping with the arrangement direction indication parts in a normal arrangement state be provided in a base sheet through which a back side can be seen.

Thus, with the teeth arranged on the maxillary plate and the mandibular plate, only by positioning the arrangement confirmation sheets to the vestibular lateral surface or the oral lateral surface, it can be easily checked whether the teeth are arranged in normal state or not. If there is an error in arrangement, it can be adjusted easily. The teeth may be arranged easily without requiring advanced skills and experiences.

According to the artificial teeth of the present invention, since the arrangement direction indication parts are extended in the apical-cervical direction or the mesiodistal direction, when arranging the teeth adjacently in the mesiodistal direction, or when arranging the maxillary teeth and mandibular teeth up and down, the teeth can be adjusted and arranged in the specified arrangement direction without requiring advanced skills and experiences.

BRIEF DESCRIPTION OF THE DRAWINGS

Further objects and advantages of the present invention will become clear from the following description taken in conjunction with the preferred embodiments thereof with reference to the accompanying drawings, in which:

FIGS. 9A and 9B are vestibular side views showing an arrangement checking method of maxillary teeth in the fourth embodiment; and FIGS. 10A and 10B are vestibular side views showing an arrangement checking method of mandibular teeth in the fourth embodiment.

DESCRIPTION OF THE PREFERRED EMBODIMENTS

An embodiment of the present invention is described with reference to the accompanying drawings.

The present invention relates to techniques of making artificial teeth as a dental prosthetic appliance of denture. A first embodiment relates to techniques to be used in making artificial molar teeth. The artificial molar teeth include a first molar tooth, a second molar tooth, a first premolar tooth, and a second premolar tooth, and preferably two or more adjacent teeth thereof may be combined, and more preferably all four adjacent teeth may be combined. Moreover, four teeth including upper and lower mutually opposing antagonist first molar teeth, antagonist second molar teeth, antagonist first premolar teeth, and antagonist second premolar teeth are preferred, and more preferably eight teeth of all upper and lower opposing molar teeth may be combined.

Figure 1:
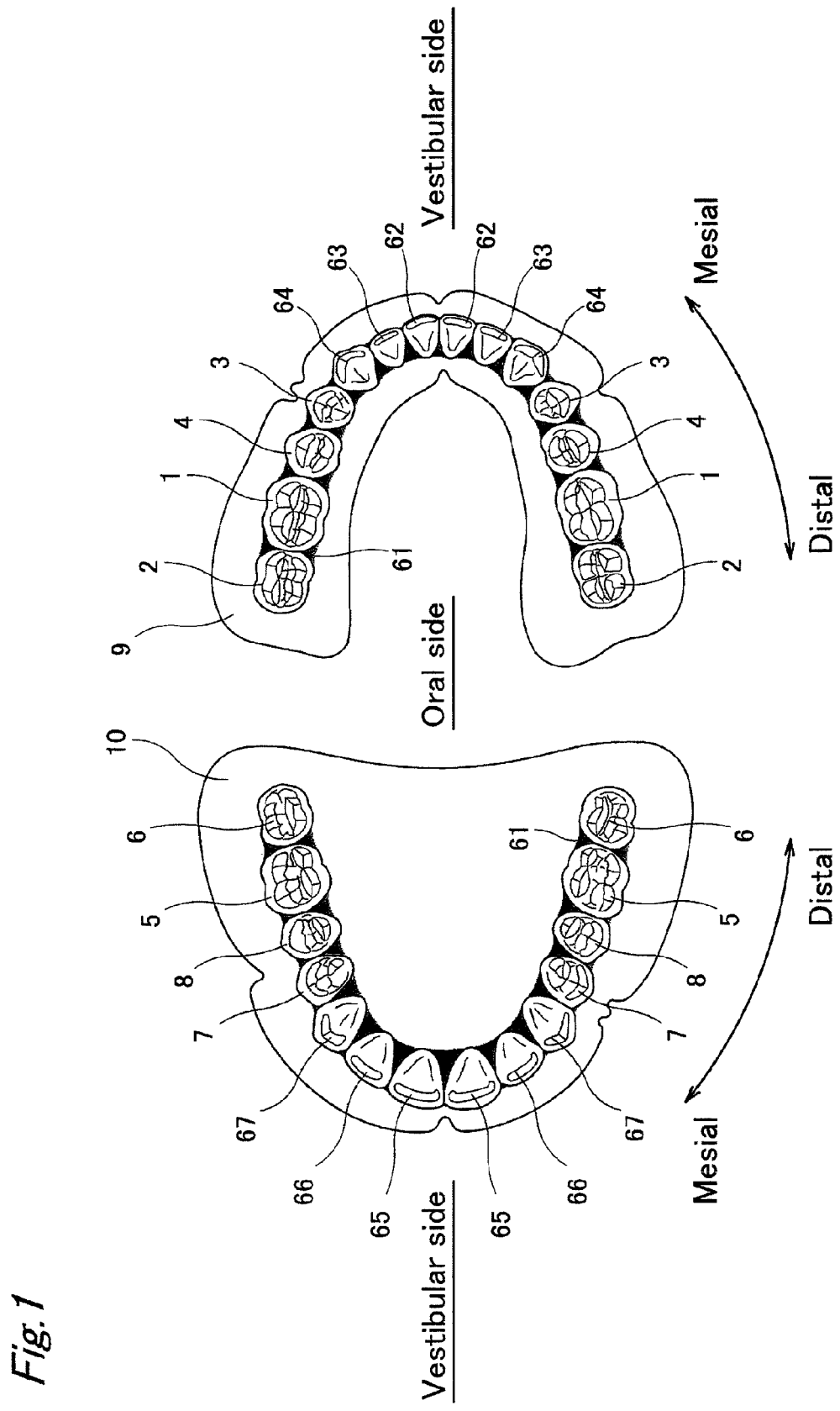
FIG. 1 is a plan view showing a basic configuration of artificial molar teeth to be arranged in the upper jaw and lower jaw.
Figure 2:
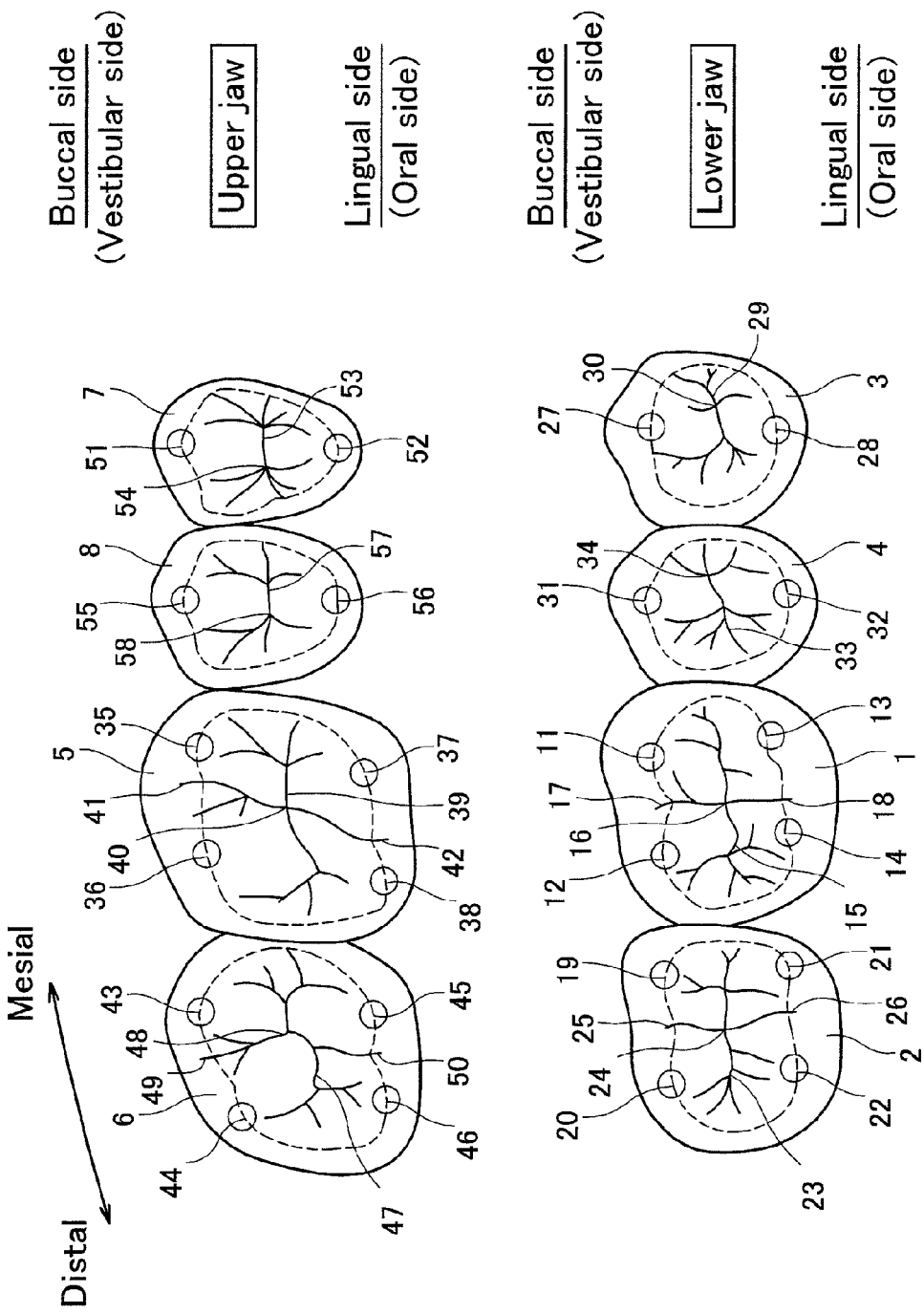
FIG. 2 is a plan view of upper molar teeth and lower molar teeth arranged and positioned up and down.

In the following description, a direction approaching anterior teeth is called a mesial side, and an opposite departing direction is called a distal side. In addition, the inside of an oral cavity is called a lingual side and a palatine side (oral side), and the outside of the oral cavity is called a buccal side and a labial side (vestibular side). The occlusal surface side of teeth is called a cuspal side (apical side), and a tooth root side is called a cervical side. FIGS. 1 and 2, which will be referred to in the following description, show a basic configuration of artificial molar teeth, in which the outline profile thereof or the like is adjusted according to each patient. The broken line in FIG. 2 shows the ridge of each molar tooth, and the inside is the occlusal plane, and the outside is the outer circumference.

FIG. 1 shows artificial teeth using artificial molar teeth in a first embodiment of the present invention. The artificial molar teeth include a mandibular first molar tooth 1, a mandibular second molar tooth 2, a mandibular first premolar tooth 3, and a mandibular second premolar tooth 4 arranged in the lower jaw, and a maxillary first molar tooth 5, a maxillary second molar tooth 6, a maxillary first premolar tooth 7, and a maxillary second premolar tooth 8 arranged in the opposed upper jaw. The lower molar teeth 1 to 4 are arranged in a mandibular plate 9, and the upper molar teeth 5 to 8 are arranged in a maxillary plate 10, and they are detachably attached in the oral cavity of the patient through these plates 9, 10. The mandibular plate 9 is formed in a generally U-shape to permit the tongue of the patient to project.

FIG. 2 shows the relation of the lower molar teeth 1 to 4 and the upper molar teeth 5 to 8 arranged on the plates 9, 10 as seen from the maxillary direction in the present embodiment. The upper side is a view of the upper molar teeth 5 to 8 as seen from the maxillary direction, and the lower side is a view of the lower molar teeth 1 to 4 as seen from the maxillary direction. However, since the occlusion state of the upper jaw is not known when seen from the maxillary direction, in order to show the state of occlusion, the occlusal surface as seen from above is shown. In the drawing, a circle "○" mark shows the cusp point of each cusp.

As shown in the figure, the mandibular first molar tooth 1 is provided with a mesial buccal cusp 11 at the mesial side of the buccal side, a distal buccal cusp 12 at the distal side of the buccal side, a mesial lingual cusp 13 at the mesial side of the lingual side, and a distal lingual cusp 14 at the distal side of the lingual side. This mandibular first molar tooth 1 may be further provided with one cusp at the distal side. These cusps 11 to 14 are lumps of tooth substance formed in a shape raised like a taper. The mandibular first molar tooth 1 has a central groove 15 extending in the mesiodistal direction formed between each pair of the buccal cusps 11, 12 and the lingual cusps 13, 14. At a specified position on the central groove 15, a central fossa 16 is formed, which reaches the maximum depth in the vertical direction in the arranged state. The mandibular first molar tooth 1 is also provided with a buccal groove 17 and a lingual groove 18 provided between each pair of the mesial cusps 11, 13 and the distal cusps 12, 14. These grooves 17, 18 are large grooves extending from the central groove 15 and the central fossa 16 to the buccal face and the lingual face, and they are extended from the cuspal side to the cervical side on the buccal face and the lingual face.

The mandibular second molar tooth 2 is provided with a mesial buccal cusp 19 at the mesial side of the buccal side, a distal buccal cusp 20 at the distal side of the buccal side, a mesial lingual cusp 21 at the mesial side of the lingual side, and a distal lingual cusp 22 at the distal side of the lingual side. These cusps 19 to 22 are lumps of tooth substance formed in a shape raised like a taper. The mandibular second molar tooth 2 has a central groove 23 extending in the mesiodistal direction formed between each pair of the buccal cusps 19, 20 and the lingual cusps 21, 22. At a specified position on the central groove 23, a central fossa 24 is formed. Further, the mandibular second molar tooth 2 is also provided with a buccal groove 25 and a lingual groove 26, similarly to those in the mandibular first molar tooth 1, formed between each pair of the mesial cusps 19, 21 and the distal cusps 20, 22.

The mandibular first premolar tooth 3 is provided with one buccal cusp 27 at the buccal side, and one lingual cusp 28 at the lingual side. These cusps 27 and 28 are lumps of tooth substance formed in a shape raised like a taper. The mandibular first premolar tooth 3 has a central groove 29 extending in the mesiodistal direction formed between the buccal cusps 27, 28, and a fossa 30 is formed at a specified position on this central groove 29.

The mandibular second premolar tooth 4 is provided with one buccal cusp 31 at the buccal side, and one lingual cusp 32 at the lingual side. These cusps 31 and 32 are lumps of tooth substance formed in a shape raised like a taper. The mandibular second premolar tooth 4 has a central groove 33 extending in the mesiodistal direction formed between the buccal cusps 31, 32, and a fossa 34 is formed at a specified position on this central groove 33.

In these mandibular premolar teeth 3, 4, buccal grooves 17, 25 or lingual grooves 18, 26 are not formed, as in the mandibular molar teeth 1, 2. However, when the pair of premolar teeth 3, 4 are made as connected teeth, a lateral groove such as lingual groove or buccal groove is formed in the connected portion. Hence, the lateral groove formed in the connected teeth is configured like the buccal grooves 17, 25 and the lingual grooves 18, 26 of the molar teeth 1, 2.

On the other hand, the maxillary first molar tooth 5 is provided with a mesial buccal cusp 35 at the mesial side of the buccal side, a distal buccal cusp 36 at the distal side of the buccal side, a mesial lingual cusp 37 at the mesial side of the lingual side, and a distal lingual cusp 38 at the distal side of the lingual side. These cusps 35 to 38 are lumps of tooth substance formed in a shape raised like a taper. The maxillary first molar tooth 5 has a central groove 39 extending in the mesiodistal direction formed between each pair of the buccal cusps 35, 36 and the lingual cusps 37, 38, and a central fossa 40 is formed at a specified position on the central groove 39. The maxillary first molar tooth 5 is also provided with a buccal groove 41 and a lingual groove 42 provided between each pair of the mesial cusps 35, 37 and the distal cusps 36, 38, similarly to those in the mandibular molar teeth 1, 2.

The maxillary second molar tooth 6 is provided with a mesial buccal cusp 43 at the mesial side of the buccal side, a distal buccal cusp 44 at the distal side of the buccal side, a mesial lingual cusp 45 at the mesial side of the lingual side, and a distal lingual cusp 46 at the distal side of the lingual side. These cusps 43 to 46 are lumps of tooth substance formed in a shape raised like a taper. The maxillary second molar tooth 6 has a central groove 47 extending in the mesiodistal direction formed between each pair of the buccal cusps 43, 44 and the lingual cusps 45, 46, and at a specified position on the central groove 47, a central fossa 48 is formed. Further, the maxillary second molar tooth 6 is also provided with a buccal groove 49 and a lingual groove 50, similarly to those in the molar teeth 1, 2, 5, formed between each pair of the mesial cusps 43, 45 and the distal cusps 44, 46.

The maxillary first premolar tooth 7 is provided with one buccal cusp 51 at the buccal side, and one lingual cusp 52 at the lingual side. These cusps 51 and 52 are lumps of tooth substance formed in a shape raised like a taper. The maxillary first premolar tooth 7 has a central groove 53 extending in the mesiodistal direction formed between the buccal cusps 51, 52, and a fossa 54 is formed at a specified position on this central groove 53.

The maxillary second premolar tooth 8 is provided with one buccal cusp 55 at the buccal side, and one lingual cusp 56 at the lingual side. These cusps 55 and 56 are lumps of tooth substance formed in a shape raised like a taper. The maxillary second premolar tooth 8 has a central groove 57 extending in the mesiodistal direction formed between the buccal cusps 55, 56, and a fossa 58 is formed at a specified position on this central groove 57.

In these maxillary premolar teeth 7, 8, as in the mandibular premolar teeth 3, 4, buccal grooves 41, 49 or lingual grooves 42, 50 are not formed, as in the maxillary molar teeth 5, 6. However, when the pair of premolar teeth 7, 8 are made as connected teeth, the lateral groove formed in the connection portion is configured like the buccal grooves 41, 49 and the lingual grooves 42, 50 of the molar teeth 5,6.

These molar teeth 1 to 8 have a curved surface on the outer circumference. Out of the outer circumference, as indicated by a single-dot chain line in FIG. 3, the most swollen and bulged portion of the molar teeth 1 to 8 in the arranged state forms a maximum contour ridge line 59. This maximum contour ridge line 59 consists of a peak of bulged curved surface, and is not a visually recognized linear form. The maximum contour ridge line 59 of the present embodiment is formed to be generally parallel and linear in the mesiodistal direction when seen from the buccal side of the molar teeth 1 to 8. Each maximum contour ridge line 59 of the molar teeth 1 to 4, 5 to 8 is provided so as to coincide in the height in the cuspal-cervical direction, so as to be positioned linearly to the mesiodistal direction when seen from the buccal side.

When the molar teeth 1 to 4, 5 to 8 having such maximum contour ridge lines 59 are arranged in the plates 9, 10, one point on the maximum contour ridge line 59 among the adjacent surfaces of the adjacent teeth 1 to 4, 5 to 8 contacts with each other. In other words, the molar teeth 1 to 4, 5 to 8 are formed and arranged in the curved surface shape so that one point on the maximum contour ridge line 59 may be contact point 60.

In the embodiment, the buccal grooves 17, 25, 41, 49 and the lingual grooves 18, 26, 42, 50 of the molar teeth 1, 2, 5, 6 are configured so that the end portion of the cervical side may be positioned on the maximum contour ridge line 59. Specifically, the buccal grooves 17, 25, 41, 49 and lingual grooves 18, 26, 42, 50 are extended from the occlusal surface to the buccal side and the lingual side in a state arranged in the plates 9, 10, and are formed to extend in the cuspal-cervical direction toward the maximum contour ridge line 59 at the buccal side and the lingual side. As a result, the cervical side end portions of the buccal grooves 17, 25, 41, 49 and lingual grooves 18, 26, 42, 50 are configured to be on a plane generally parallel to the mesiodistal direction with the contact point 60 with the adjacent teeth in the arranged state. The buccal grooves 17, 25, 41, 49 are provided generally in parallel as seen from the buccal side in a three-dimensionally manner, and the lingual grooves 18, 26, 42, 50 are provided generally in parallel as seen from the lingual side. Hence, the buccal grooves 17, 25 of the mandibular molar teeth 1, 2 are positioned in parallel to the buccal grooves 41, 49 of the maxillary molar teeth 5, 6, and the lingual grooves 18, 26 of the mandibular molar teeth 1, 2 are positioned in parallel to the lingual grooves 42, 50 of the maxillary molar teeth. The buccal grooves 17, 25, 41, 49 and lingual grooves 18, 26, 42, 50 positioned at the buccal side and the lingual side may be curved in a side view as long as they are extended in parallel, but are preferred to be linear extending in the cuspal-cervical direction in a side view.

Figure 3:
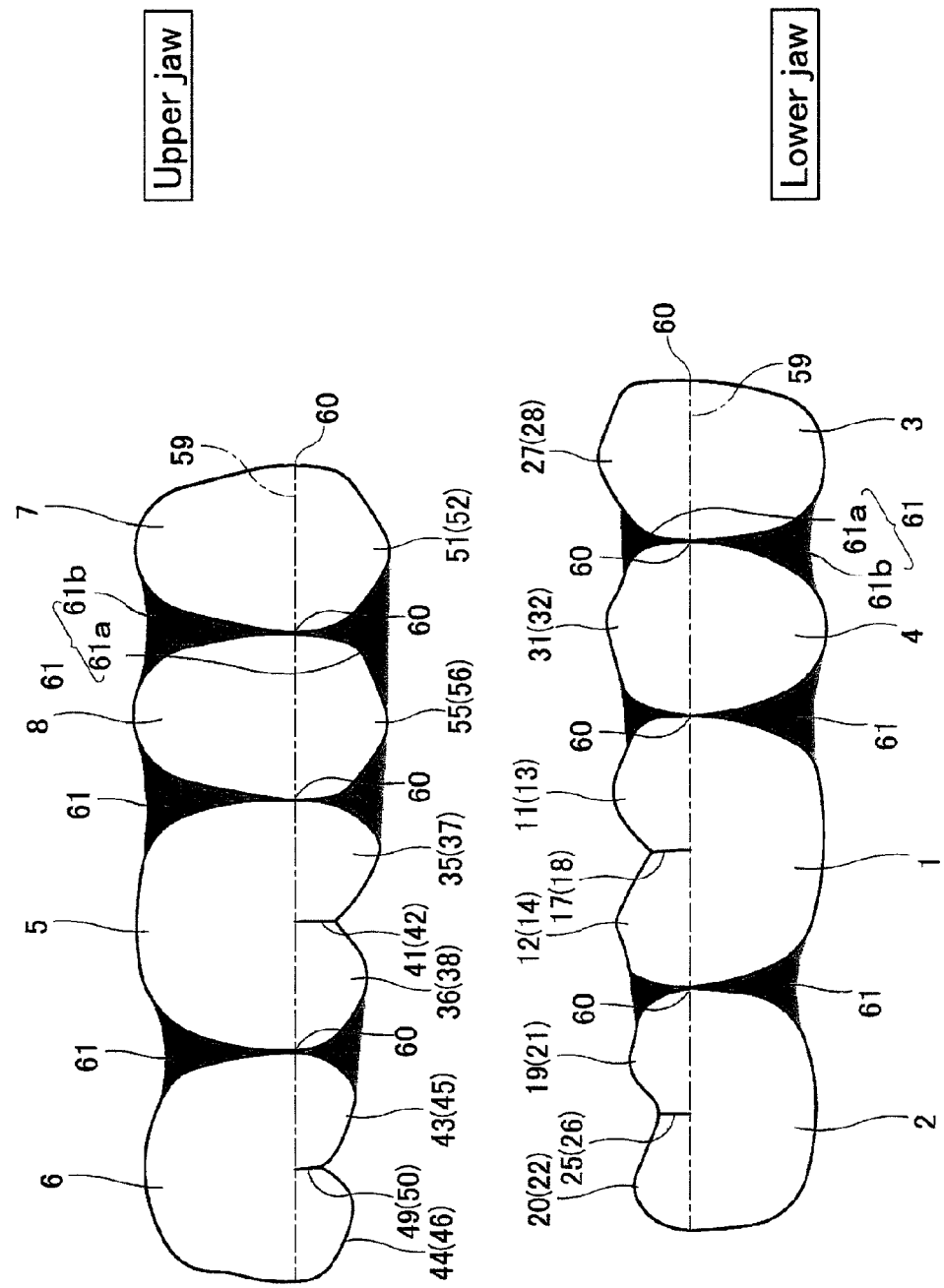
FIG. 3 is a buccal side view showing an up-and-down arranged state of upper molar teeth and lower molar teeth in a first embodiment.

The molar teeth 1 to 4, 5 to 8 are indicated by gray shading in FIGS. 1 and 3, in which an embrasure 61 formed of hourglass or shoulder-drum shaped gaps (space) is formed between adjacent teeth in the state arranged in the plates 9, 10. As shown in FIG. 3, this embrasure 61 is divided into a cusp embrasure 61a positioned at the cuspal side from the contact point 60, and a cervical embrasure 61b positioned at the cervical side from the contact point 60. Accordingly, when the molar teeth 1 to 4, 5 to 8 are arranged, in a buccal side view, the bottom (depth) of the cusp embrasure 61a coincides with the maximum contour ridge line 59. That is, the depth of the cusp embrasure 61a is configured so that the height in the cuspal-cervical direction may coincide in the mesiodistal direction with the cervical side end portions of the buccal grooves 17, 25, 41, 49 and lingual grooves 18, 26, 42, 50.

In the molar teeth 1 to 4, 5 to 8 thus composed, the extending direction of the buccal grooves 17, 25, 41, 49 and lingual grooves 18, 26, 42, 50 is used as an arrangement direction indication part for instructing the direction of arrangement in line and in parallel. The cervical side end portions of the buccal grooves 17, 25, 41, 49 and the lingual grooves 18, 26, 42, 50, and the maximum contour ridge line 59 including the contact point 60 are used as an arrangement direction indication part for instructing the arrangement direction (position) in the cuspal-cervical direction between adjacent teeth.

A description is given below of an operation of arranging the molar teeth 1 to 8 having the above configuration in the plates 9, 10. In the completed dentures, the plates 9, 10 are made of resin. The resin-made plates are formed in place of the wax rims as temporary plates after arrangement of artificial teeth. More specifically, the wax rims are made of wax as temporary plates from patterns taken from a patient, and the artificial teeth are arranged in the wax rims to make temporary dentures. The temporary dentures are covered with plaster, and the wax rim is melted away, and the resin is injected, so that resin-made plates 9, 10 are formed, and the completed dentures are taken out from the plaster.

First, in the mandibular plate 9 arranged with a lower central incisor 62, a lower lateral incisor 63, and a lower canine 64, the mandibular first premolar tooth 3 is arranged at the distal side of the lower canine 64. At this time, the mandibular first premolar tooth 3 is arranged so that the contact point 60 contacts with the lower canine 64 and the height of the peak of the cusps 27, 28 may coincide with that of the top of the lower canine 64 in the apical-cervical direction.

Next, the mandibular second premolar tooth 4 is arranged in the mandibular plate 9. At this time, the positions of the cusps 31, 32 of the mandibular second premolar tooth 4 in the buccal-lingual direction are arranged to correspond to the cusps 27, 28 of the mandibular first premolar tooth 3. The mandibular second premolar tooth 4 is arranged with respect to the mandibular first premolar tooth 3 so that the heights in the cuspal-cervical direction of the mutual maximum contour ridge lines 59, 59 coincide with each other and the mutual contact points 60, 60 contact with each other.

The mandibular first molar tooth 1 is arranged next in the mandibular plate 9. At this time, the positions of the buccal cusps 11, 12 and the lingual cusps 13, 14 of the mandibular first molar tooth 1 in the buccal-lingual direction are arranged to correspond to the buccal cusp 31 and the lingual cusp 32 of the mandibular second premolar tooth 4. The mandibular first molar tooth 1 is arranged with respect to the mandibular second premolar tooth 4 so that the height in the cuspal-cervical direction of the mutual maximum contour ridge lines 59, 59 may coincide with each other. The cervical side end portion of the buccal groove 17 or lingual groove 18, the mesial side contact point 60 of the mandibular first molar tooth 1, and the contact point 60 of the adjacently arranged mandibular premolar teeth 3,4 are arranged so as to be positioned at the height in each cuspal-cervical direction linearly in the mesiodistal direction.

Next, the mandibular second molar tooth 2 is arranged in the mandibular plate 9. At this time, the positions of the buccal cusps 19, 20 and the lingual cusps 21, 22 of the mandibular second molar tooth 2 in the buccal-lingual direction are arranged to correspond to the buccal cusps 11, 12 and the lingual cusps 13,14 of the mandibular first molar tooth 1. The mandibular second molar tooth 2 is arranged with respect to the mandibular first molar tooth 1 so that the buccal groove 25 and the lingual groove 26 are positioned in parallel to the buccal groove 17 and the lingual groove 18 of the mandibular first molar tooth 1, and the heights in the cuspal-cervical direction of the mutual maximum contour ridge lines 59, 59 coincide with each other. The cervical side end portions of the buccal groove 25 and the lingual groove 26 and the mesial side contact point 60 of the mandibular second molar tooth 2 and the cervical side end portions of the buccal groove 17 and the lingual groove 18 of the adjacently arranged mandibular first molar tooth 1 are arranged so that the heights in each cuspal-cervical direction of them are positioned linearly in the mesiodistal direction.

Similarly, the maxillary first premolar tooth 7 is arranged in the maxillary plate 10 arranged with an upper central incisor 65, an upper lateral incisor 66, and an upper canine 67. At this time, the maxillary first premolar tooth 7 is arranged so that the contact point 60 contacts with the upper canine 60 and the heights of the peaks of the cusps 51, 52 may coincide with that of the apex of the upper canine 67 in the apical-cervical direction.

The maxillary second premolar tooth 8 is arranged in the maxillary plate 10. At this time, the positions of the cusps 55, 56 of the maxillary second premolar tooth 8 in the buccal-lingual direction are arranged to correspond to the cusps 51, 52 of the maxillary first premolar tooth 7. The maxillary second premolar tooth 8 is arranged with respect to the maxillary first premolar tooth 7 so that the heights of mutual maximum contour ridge lines 59, 59 coincide with each other in the cuspal-cervical direction, and the mutual contact points 60, 60 contact with each other.

The maxillary first molar tooth 5 is arranged in the maxillary plate 10. At this time, the positions of the buccal cusps 35, 36 and the lingual cusps 37, 38 of the maxillary first molar tooth 5 in the buccal-lingual direction are arranged to correspond to the buccal cusp 55 and the lingual cusp 56 of the maxillary second premolar tooth 8. The maxillary first molar tooth 5 is arranged with respect to the maxillary second premolar tooth 8 so that the mutual maximum contour ridge lines 59, 59 coincide with each other in the cuspal-cervical direction. The cervical side end portion of the buccal groove 41 or the lingual groove 42 and the mesial side contact point 60 of the maxillary first molar tooth 5, and the contact points 60 of the adjacently arranged maxillary premolar teeth 5, 6 are arranged so as to coincide in the height in each cuspal-cervical direction linearly in the mesiodistal direction.

Finally, the maxillary second molar tooth 6 is arranged in the maxillary plate 10. At this time, the positions of the buccal cusps 43, 44 and the lingual cusps 45, 46 of the maxillary second molar tooth 6 in the buccal-lingual direction are arranged to correspond to the buccal cusps 35, 36 and the lingual cusps 37, 38 of the maxillary first molar tooth 5. The maxillary second molar tooth 6 is arranged with respect to the maxillary first molar tooth 5 so that the buccal groove 49 and the lingual groove 50 are positioned in parallel to the buccal groove 41 and the lingual groove 42 of the maxillary first molar tooth 5 and the height in the cuspal-cervical direction of the mutual maximum contour ridge lines 59, 59 may coincide with each other. The cervical side end portion of the buccal groove 49 or the lingual groove 50 of the maxillary second molar tooth 6, and the mesial side contact point 60, and the cervical side end portion of the buccal groove 41 or the lingual groove 42 of the adjacently arranged maxillary first molar tooth 5 are arranged so that the heights in each cuspal-cervical direction of them are positioned linearly in the mesiodistal direction.

Incidentally, when the mandibular premolar teeth 3, 4 and/or maxillary premolar teeth 5, 6 are formed integrally as connected teeth, the buccal groove or the lingual groove formed in the connected teeth is positioned in parallel to the buccal grooves 17, 42 or the lingual grooves 18, 43 of the mandibular first molar tooth 1 and/or maxillary first molar tooth 5, and the height of the mutual cervical side end portions in the cuspal-cervical direction is coincided in the mesiodistal direction. Thus arranged lower molar teeth 1 to 4 and upper molar teeth 5 to 8 are mutually occluded, and the arrangement position in the mesiodistal direction and the buccal-lingual direction is adjusted.

In the present invention, therefore, including the case of making the premolar teeth 3,4 and 7, 8 as the connected teeth, the buccal grooves 17, 25, 41, 49 and lingual grooves 18, 26, 42, 50 of the molar teeth 1, 2, 5, 6 are formed as the arrangement direction indication parts. Accordingly, only by arranging the buccal grooves 17, 25, 41, 49 and lingual grooves 18, 26, 42, 50 so as to extend in parallel, the molar teeth 1 to 4, 5 to 8 adjacent in the mesiodistal direction may be arranged easily and securely in a specified directivity. Moreover, in the embodiment, the cervical side end portions of the buccal grooves 17, 25, 41, 49 and lingual grooves 18, 26, 42, 50 of the molar teeth 1, 2, 5, 6 are configured to be positioned on the maximum contour ridge line 59. Moreover, the contact points with the adjacent teeth are formed on a plane generally parallel to the mesiodistal direction. Accordingly, by arranging so that the cervical side end portions of the buccal grooves 17, 25, 41, 49 and lingual grooves 18, 26, 42, 50 and the contact points 60 may be formed linearly in the mesiodistal direction, the height in the cuspal-cervical direction may be adjusted securely.

Accordingly, when arranging the lower molar teeth 1 to 4 and upper molar teeth 5 to 8 in the mandibular plate 9 and the maxillary plate 10, without requiring advanced skills and experiences, the teeth can be arranged at appropriate positions according to the oral cavity environment of each patient. Specifically, the oral cavity of patient is very large in individual difference, and in clinical cases of edentulous jaw, the space, the alveolar ridge height, and angle in the oval cavity are largely different, and in such varied clinical cases, the artificial molar teeth can be arranged easily and in a short time, and the situation in the oral cavity can be reproduced. Besides, since the artificial teeth are arranged on the wax rim as temporary plate, it has been difficult to understand the positional relation of mutual artificial teeth, but the situation can be understood easily. In addition, since the correct arrangement position can be easily determined, the arrangement working efficiency is notably enhanced. Since accurate arrangement is possible, mastication is easily achieved after fabrication of the dentures, and in addition to the cutting function, grinding function can be added. Moreover, the oral cavity looks aesthetic after attachment of the prosthesis.

Figure 4:
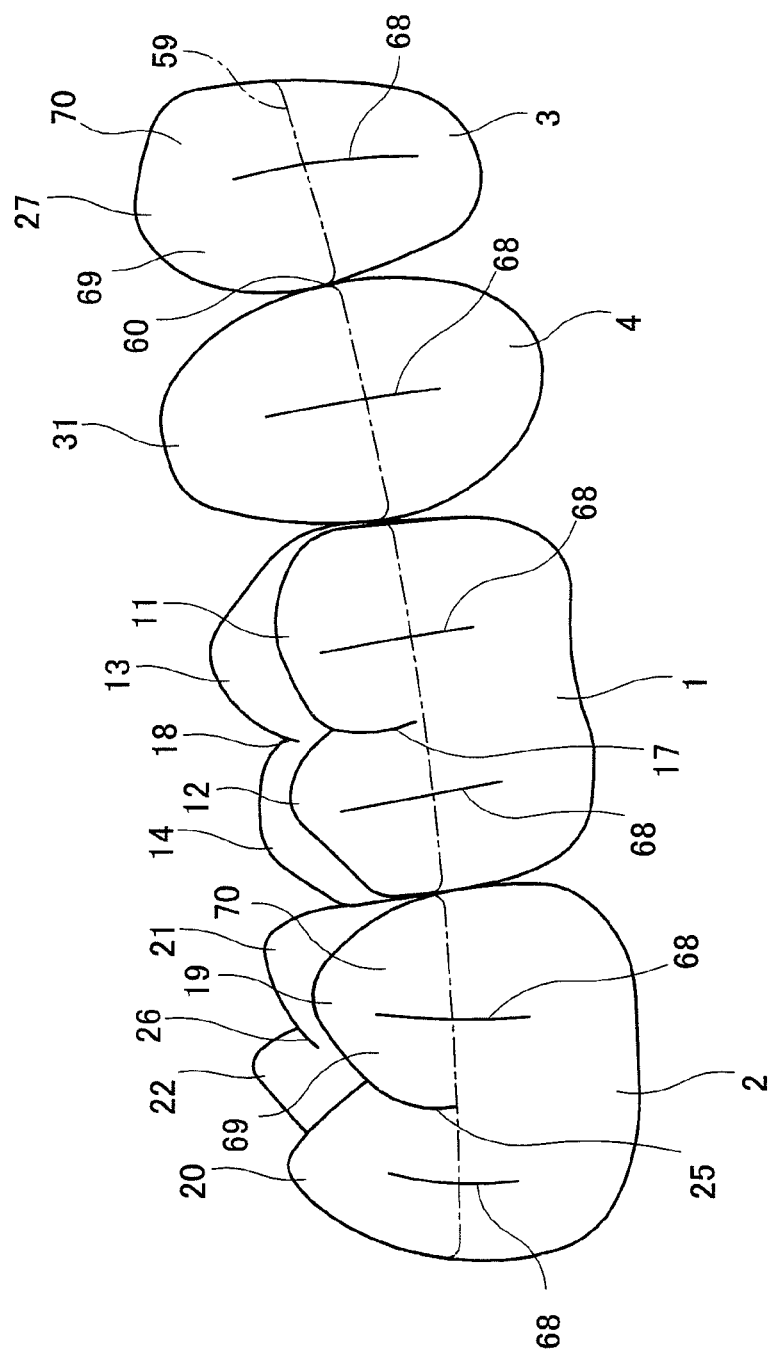
FIG. 4 is a perspective view of state of molar teeth arranged along arrangement direction indication lines in a second embodiment.
Figure 5:
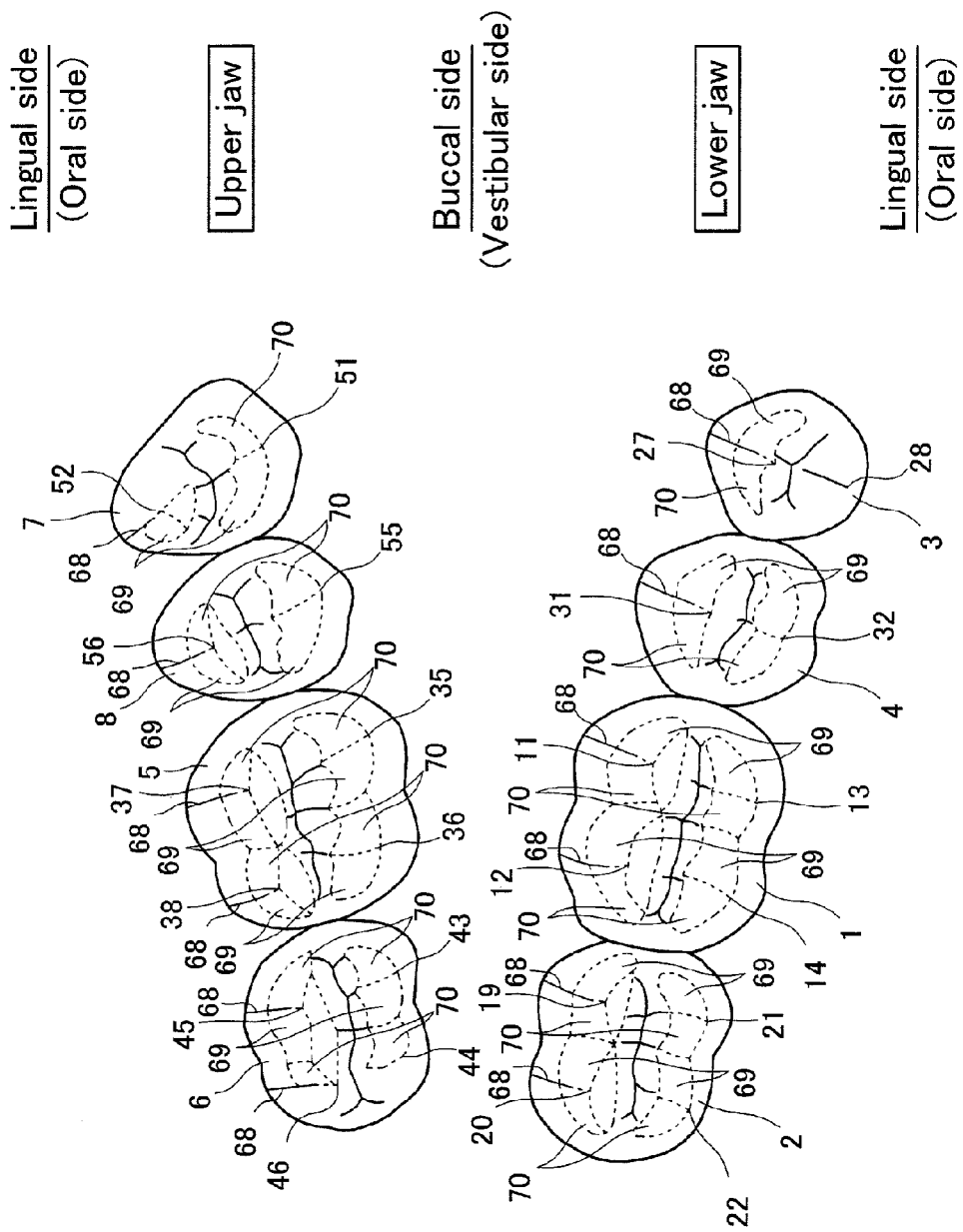
FIG. 5 is a plan view for explaining the forming concept of arrangement direction indication lines in the second embodiment.

FIGS. 4 and 5 show molar teeth 1 to 4, 5 to 8 in a second embodiment. This second embodiment is different from the first embodiment in that as the arrangement direction indication parts there are provided arch expressing parts 68 which are positioned near the maximum contour ridge lines 59 and consist of ridge lines appearing as surface shapes of molar teeth 1 to 4, 5 to 8 on a plane vertical to the maximum contour ridge lines 59, and that the arch expressing parts 68 are arranged in parallel. The arch expressing parts 68 are continued to the boundary lines of facets 69, 70 formed at the mesial side and the distal side at each cusp of the molar teeth 1 to 4, 5 to 8, as shown in FIG. 5.

More specifically, in the lower molar teeth 1 to 4, anterior occlusal facets 69 involved in the balancing function and masticatory function in lateral motion or intermediate motion are formed on the mesial-buccal side of the buccal cusps 11, 12, 19, 20, 27, 31, and on the mesial-buccal side of the lingual cusps 13, 14, 21, 22, 28, 32. The lower molar teeth 1 to 4 are also provided with posterior occlusal facets 70 involved in the masticatory function in lateral motion or posterior motion formed on the distal-buccal side of the buccal cusps 11, 12, 19, 20, 27, 31, and on the distal-buccal side of the lingual cusps 13, 14, 21, 22, 28, 32. Between these anterior occlusal facets 69 and posterior occlusal facets 70, the arch expressing parts 68 which rise in the buccal direction due to difference in the curvature and extend in the cuspal-cervical direction are formed. Of them, the arch expressing parts 68 formed at the buccal side of the buccal cusps 11, 12, 19, 20, 27, 31 form the arrangement direction indication parts extending respectively in parallel.

In the upper molar teeth 5 to 8, anterior occlusal facets 69 are formed on the distal-lingual side of the buccal cusps 35, 36, 43, 44, 51, 55, and on the distal-lingual side of the lingual cusps 37, 38, 45, 46, 52, 55. Further, posterior occlusal facets 70 are formed on the mesial-lingual side of the buccal cusps 35, 36, 43, 44, 51, 55, and on the mesial-lingual side of the lingual cusps 37, 38, 45, 46, 52, 55. Between these anterior occlusal facets 69 and posterior occlusal facets 70, the arch expressing parts 68 are formed as in the lower molar teeth 1 to 4. Of them, the arch expressing parts 68 formed at the lingual side of the lingual cusps 37, 38, 45, 46, 52, 55 form the arrangement direction indication parts extending respectively in parallel.

The arch expressing parts 68 formed in this manner are formed in each pair at the buccal side of the mandibular molar teeth 1, 2, and in one piece at the buccal side of the mandibular premolar teeth 3, 4, and formed in each pair at the lingual side of the maxillary molar teeth 5, 6, and in one piece at the lingual side of the maxillary premolar teeth 7, 8. These arch expressing parts 68 may be formed of corners formed by intersection of the anterior occlusal facets 69 and the posterior occlusal facets 70, but may be preferably formed as curved peak parts. The arch expressing parts 68 may be also formed preferably continuously in a band form from the cuspal peak to the cervical part, but may be formed discontinuously in the cuspal-cervical direction. In this case, at least in the region where the maximum contour ridge line 59 is formed, preferably, the arch expressing parts 68 may be formed continuously in a band form so as to intersect with the maximum contour ridge lines 59. When the arch expressing parts 68 are formed in the curved surface peaks and continuously in the cuspal-cervical direction, the arrangement working efficiency may be effectively enhanced.

In other words, when arranging the lower molar teeth 1 to 4 and the upper molar teeth 5 to 8 in the plates 9, 10, the teeth are arranged as in the first embodiment. In the case that the molar teeth 1 to 8 are arranged in a correct directivity, the arch expressing parts 68 may be visually recognized as a continuous band form. On the other hand, when the molar teeth 1 to 8 are arranged in a state inclined in the mesiodistal direction, the arch expressing parts 68 are not expressed as a continuous band form. Hence, by checking this state, an operator can recognize a deviation in the arrangement direction. When all of the molar teeth 1 to 4, 5 to 8 are arranged in a correct directivity, as shown in FIG. 4, all arch expressing parts 68 are expressed in a parallel profile. As a result, the working efficiency regarding position adjustment of the molar teeth 1 to 8 can be enhanced.

In the embodiment, the cervical side end portions of the lateral grooves 17, 18, 25, 26, 41, 42, 49, 50 of the molar teeth 1, 2, 5, 6 are positioned on the maximum contour ridge lines 59 as in the first embodiment, but only the arch expressing parts 68 may be provided as the arrangement direction indication parts.

Figure 6:
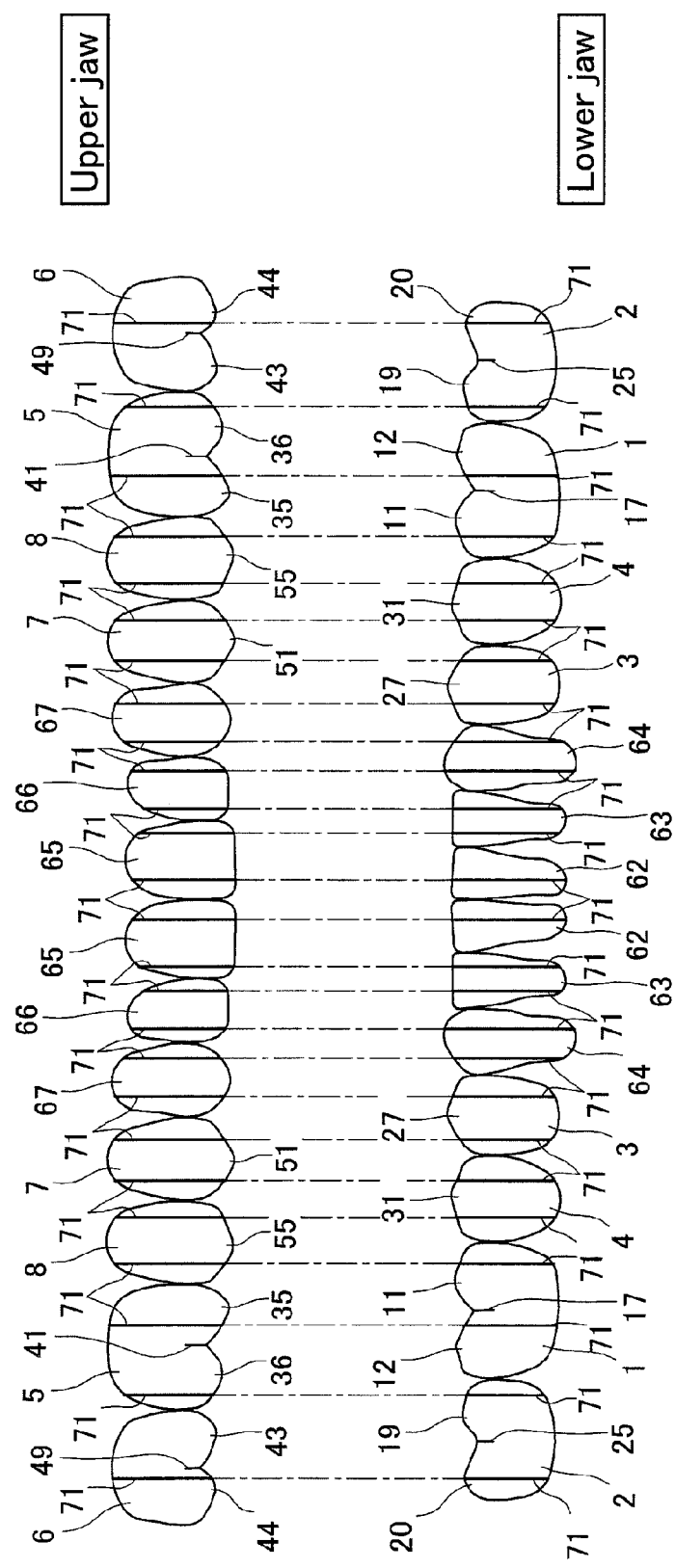
FIG. 6 is a vestibular side view showing a state of maxillary teeth and mandibular teeth arranged in a row respectively in a third embodiment.
Figure 7:
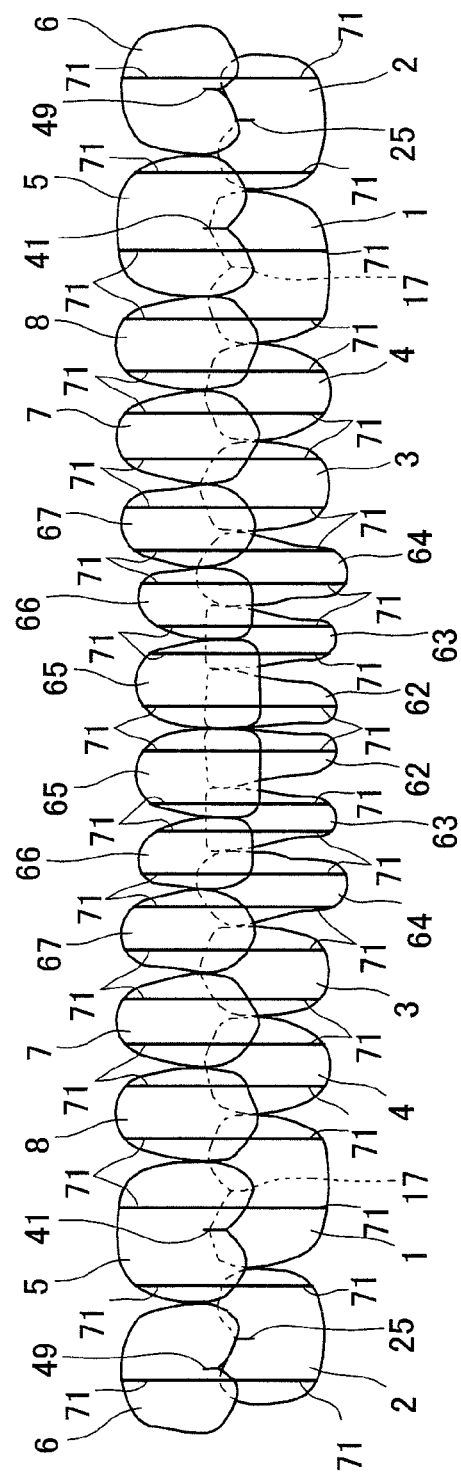
FIG. 7 is a vestibular side view showing an overlapped state of the maxillary teeth and mandibular teeth in the third embodiment.

FIGS. 6 and 7 show the artificial teeth 1 to 8, 62 to 67 in a third embodiment. The third embodiment relates to an arrangement of all artificial teeth including not only the molar teeth 1 to 8, but also anterior teeth such as lower incisors 62, 63 and a lower canine 64, and upper incisors 65, 66, and an upper canine 67, and in particular the positional relation of the antagonist upper and lower teeth 5 to 8, 65 to 67, and 1 to 4, 62 to 64 can be arranged efficiently in the specified state.

More specifically, the artificial teeth 1 to 8, 62 to 67 in the third embodiment are provided with indication lines 71 extended in the apical-cervical direction by coloring the vestibular lateral side as arrangement direction indication parts. As shown in FIG. 7, when covered in a central occlusion position, a part of the vestibular side of the mandibular teeth 1 to 4, 62 to 64 is covered with the maxillary teeth 5 to 8, 65 to 67. After the arrangement, moreover, the wax (the wax rim of the temporary plate) is replace by a resin plate (a resin-made plate). Accordingly, in order that the indication lines 71 may not be concealed in this covered state or may not be concealed by the wax, the indication lines 71 are extended linearly from the apical side edge to the cervical side edge as seen from the vestibular side. Being extended linearly means, herein, either one straight line, or a line containing plural points extended intermittently (e.g., broken line). In the embodiment, the indication lines 71 of the upper and lower antagonist teeth, that is, the maxillary teeth 5 to 8, 65 to 67, and the mandibular teeth 1 to 4, 62 to 64 are provided linearly to be positioned at the central occlusion position.

At the central occlusion position, the lower central incisor 62 is covered with the upper central incisor 65, the upper central incisor 65 further covers the lower lateral incisor 63, the lower lateral incisor 63 is further covered with the upper lateral incisor 66, the upper lateral incisor 66 further covers the lower canine 64, the lower canine 64 is further covered with the upper canine 67, the upper canine 67 further covers the mandibular first premolar tooth 3, the mandibular first premolar tooth 3 is further covered with the maxillary first premolar tooth 7, the maxillary first premolar tooth 7 further covers the mandibular second premolar tooth 4, the mandibular second premolar tooth 4 is further covered with the maxillary second premolar tooth 8, the maxillary second premolar tooth 8 further covers the mandibular first molar tooth 1, the mandibular first molar tooth 1 is further covered with the maxillary first molar tooth 5, the maxillary first molar tooth 5 further covers the mandibular second molar tooth 2, and the mandibular second molar tooth 2 is further covered with the maxillary second molar tooth 6. Accordingly, the lower central incisor 62 and the maxillary second molar tooth 6, covered by or covering only one tooth each, is provided with one indication line 71 each, so as to be positioned linearly to the indication line 71 of the antagonist teeth 65, 2 covering or to be covered. The other teeth 1 to 7, 63 to 67 to be covered with or covering these two teeth are provided with two indication lines 71 in parallel, so as to be positioned linearly to the indication lines 71 of the two teeth 1 to 8, 62 to 67 covering or to be covered.

The forming method of these indication lines 71 includes a method of coloring the forming position of the vestibular side, and a method of coloring the region excluding the forming position so as to be expressed by the non-colored region. The colored region and the non-colored region are preferred to be different in color, but a same or similar color may be possible. However, in the case of same color or transparent color, it is preferred to use a color emitting light at a specified frequency, or developing color or emitting light in darkness. When using different colors, different colors such as black, red or blue may be used in each one of the artificial teeth 1 to 8, 62 to 67, or in each one of indication lines 71.

The coloring material for forming indication lines 71 may be an oil-based ink and other material not deleted (peeled) in arrangement or transportation process. This coloring material may be naturally erased when worn in the oral cavity, or may be removed by using a chemical after the arrangement. The pigment of the coloring material may contain an organic material and a coloring material, and may preferably a material for oral use as designated as a food additive.

The artificial teeth 1 to 8, 62 to 67 of the third embodiment having the above configuration are arranged, for example, as in the first embodiment, sequentially from the lower central incisor 62 to the mandibular second molar tooth 2 in the distal direction, and arranged sequentially from the upper central incisor 65 to the maxillary second molar tooth 6. Then, after occlusion between the mandibular teeth 1 to 4, 62 to 64, and the maxillary teeth 5 to 8, 65 to 67, the indication lines 71 corresponding to each other are positioned and adjusted linearly.

Alternatively, after arranging the lower central incisor 62 in the mandibular plate 9, the upper central incisor 65 is arranged in the maxillary plate 10. After occlusion of these central incisors 62, 65, the indication line 71 positioned at the mesial side of the upper central incisor 65 and the indication line 71 of the lower central incisor 62 are adjusted to be positioned linearly. In succession, after arranging the lower lateral incisor 63 in the mandibular plate 9, the lower lateral incisor 63 and the upper central incisor are occluded, and the indication line 71 at the mesial side of the lower lateral incisor 63 and the indication line 71 at the distal side of the upper central incisor 65 are adjusted to be positioned linearly. Then, after arranging the upper lateral incisor 66 in the maxillary plate 10, the upper lateral incisor and the lower lateral incisor are occluded, and the indication line 71 at the mesial side of the upper lateral incisor 66 and the indication line 71 at the distal side of the lower lateral incisor 63 are adjusted to be positioned linearly.

In this manner, the mandibular teeth 1 to 4, 62 to 64 and the maxillary teeth 5 to 8, 65 to 67 are sequentially arranged in the plates 9, 10, and are occluded on every occasion of arrangement, and the mesial side indication lines of the later arranged teeth may be linearly positioned and adjusted to the distal side indication lines 71 of the previously arranged teeth. By repeating this operation, the teeth are arranged up to the final maxillary second molar tooth 6. When arrangement and adjustment of all teeth are completed, the indication lines 71 are removed.

As described above, since the artificial teeth 1 to 8, 62 to 67 of the third embodiment are provided with the colored indication lines 71 extended in the apical-cervical direction as the arrangement direction indication parts, only by adjusting the indication lines 71 to be positioned linearly to the mandibular teeth 1 to 4, 62 to 64 and the maxillary teeth 5 to 8, 65 to 67, the position in the mesiodistal direction can be adjusted easily without requiring advanced skills and experiences. Moreover, not limited to the molar teeth 1, 2, 5, 6 as in the first embodiment, the premolar teeth 3, 4, 7, 8 and the anterior teeth 62 to 67 can be adjusted easily. Recently, it is required to keep the record of the process of treatment, and it is easy to keep the record of the arrangement process by photographs or the like according to the third embodiment.

Figure 8:
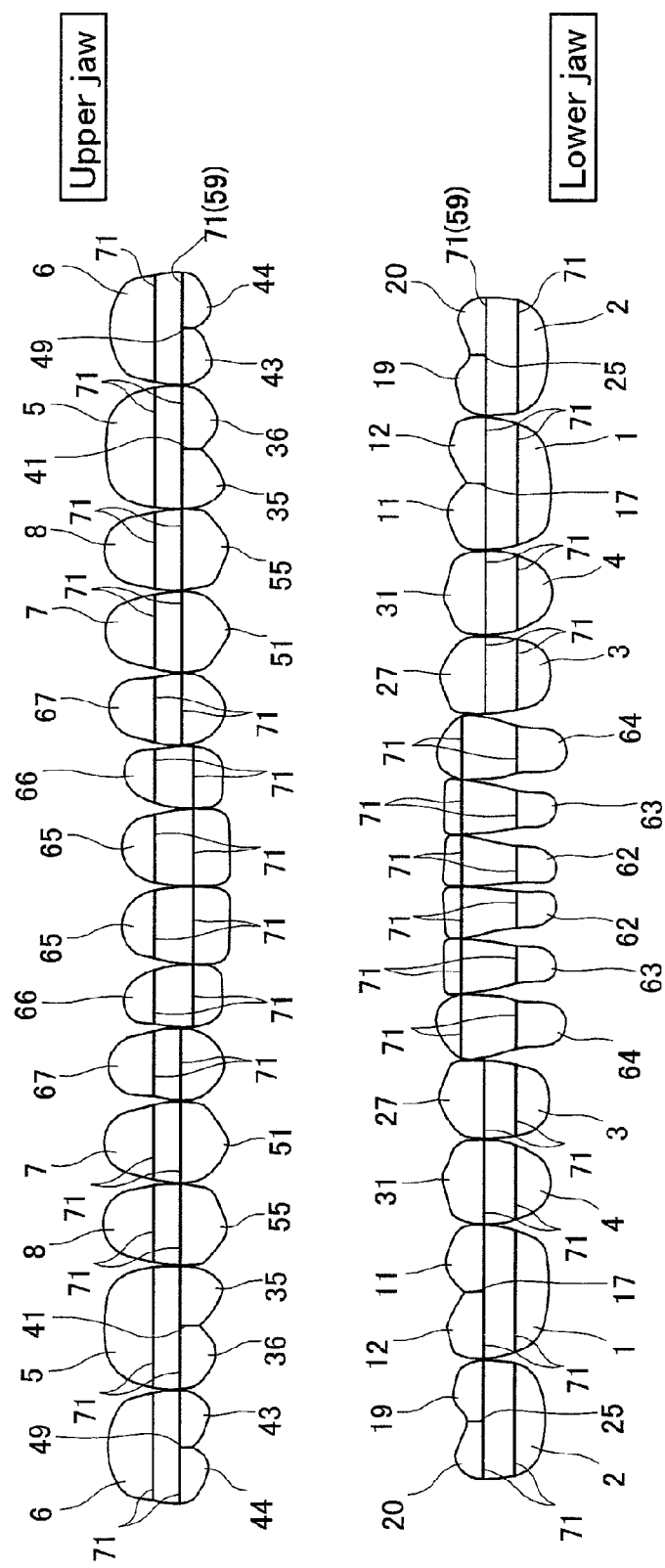
FIG. 8 is a vestibular side view showing a state of the maxillary teeth and mandibular teeth arranged in a row respectively in a fourth embodiment.

FIGS. 8 to 10 show the artificial teeth 1 to 8, 62 to 67 in a fourth embodiment. This fourth embodiment is significantly different from the third embodiment in that as the arrangement indication parts, there are provided the indication lines 71 which are formed by coloring the buccal side and are extended in the mesiodistal direction. Moreover, this embodiment differs from the foregoing embodiments in that arrangement confirmation sheets 72A, 72B are additionally provided for checking the arrangement state in the arranged state of the artificial teeth 1 to 8, 62 to 67.

More specifically, as shown in FIG. 8, the artificial teeth 1 to 8, 62 to 67 of the embodiment are provided with a pair of indication lines 71, 71, individually extended in the mesiodistal direction. One of these indication lines 71, 71 is deviated to the cervical side at one crown, and the other is deviated to the apical side. The cervical side indication line 71 in the mandibular teeth 1 to 4, 62 to 64 and in the maxillary teeth 5 to 8, 65 to 67 is provided so as to be positioned linearly all in the mesiodistal direction. The apical side indication line 71 in the mandibular teeth 1 to 4, 62 to 64 and in the maxillary teeth 5 to 8, 65 to 67 is provided so as to be positioned on the maximum contour ridge line 59.

In the embodiment, the lower molar teeth 1 to 4 and the upper molar teeth 5 to 8 are formed, as in the first embodiment, so that the maximum contour ridge lines 59 may be positioned linearly. Accordingly, the apical side indication lines 71 formed on them are positioned linearly in the mesiodistal direction. Of the other artificial teeth 62 to 67, the lower anterior teeth 62 to 64 are formed so that the maximum contour ridge line 59 may be positioned linearly in the mesiodistal direction. Hence, the apical side indication line 71 formed on them is positioned linearly in the mesiodistal direction. In the upper anterior teeth 65 to 67, except for the upper canine 67 at the distal side, the maximum contour ridge line 59 of the upper central incisor 65, 66 is formed to be positioned linearly in the mesiodistal direction. Hence, the apical side indication line 71 formed on them is positioned linearly in the mesiodistal direction. The upper canine 67 is configured so that the maximum contour ridge line 59 may be positioned linearly in the mesiodistal direction to the upper molar teeth 5 to 8. Hence, the indication line 71 of the upper canine 67 is positioned linearly to the mesiodistal direction to the apical side indication line 71 of the upper molar teeth 5 to 8.

When the mandibular teeth 1 to 4, 62 to 64 having the above configuration are arranged in normal arrangement state, a group of one indication line 71 extending intermittently at the cervical side is formed. At the apical side, a group of two indication lines 71 extending generally continuously is formed. The group of these indication lines 71 is positioned parallel to the apical-cervical direction and is extended in parallel. Similarly, when the maxillary teeth 5 to 8, 65 to 67 are arranged in normal arrangement state, a group of one indication line 71 extending intermittently at the cervical side is formed. At the apical side, a group of two indication lines 71 extending generally continuously is formed. The group of these indication lines 71 is positioned parallel to the apical-cervical direction and is extended in parallel. When the mandibular teeth 1 to 4, 62 to 64, and the maxillary teeth 5 to 8, 65 to 67 are occluded at the central occlusion position, the group of these indication lines 71 is positioned in parallel to the apical-cervical direction, and is extended in parallel.

When the artificial teeth 1 to 8, 62 to 67 of the fourth embodiment are arranged, as in the first embodiment, the mandibular teeth 1 to 4, 62 to 64 and the maxillary teeth 5 to 8, 65 to 67 are arranged sequentially in the plates 9, 10 from the central incisors 62, 65 to the distal side up to the second molar teeth 2, 6. At this time, in each upper and lower pair of central incisors 62, 62 and 65, 65, except for the previously arranged central incisors 62,65, the later arranged mandibular teeth 1 to 4, 62 to 64 and maxillary teeth 5 to 8, 65 to 67 are arranged by adjusting so that the indication lines 71, 71 positioned at the apical side and the cervical side may be positioned linearly in the mesiodistal direction with respect to the indication lines 71, 71 of the previously arranged teeth. The mandibular teeth 1 to 4, 62 to 64 and the maxillary teeth 5 to 8, 65 to 67 are adjusted and arranged so that the indication lines 71, 71 may be extended in parallel. As a result, as in the foregoing embodiments, without requiring advanced skills and experiences, the teeth may be arranged in specified positions by adjusting the position in the mesiodistal direction and the apical-cervical direction.

In the embodiment, when arrangement of the artificial teeth 1 to 8, 62 to 67 in the plates 9, 10 is completed, as shown in FIGS. 9A, 9B and FIGS. 10A, 10B, the arrangement state is confirmed by the arrangement confirmation sheets 72A, 72B. The arrangement confirmation sheets 72A, 72B are formed of a base sheet 73, and confirm lines 74 to be overlapped with indication lines 71 in the normally arranged state. In this embodiment, two types are provided, for the mandibular teeth 1 to 4, 62 to 64, and the maxillary teeth 5 to 8, 65 to 67. The base sheet 73 is transparent or translucent so that the back side may be visible. The base sheet 73 is rectangular in shape formed of an elastically deformable resin. The confirm line 74 is formed in a line width similar to the indication line 71, and is opaque so that the back side may not be visible. The confirm line 74 is formed of an oil-based ink similar to the indication line 71, or formed of an opaque resin by double mold.

The arrangement confirmation sheet 72A is disposed at the vestibular side of the arranged mandibular teeth 1 to 4, 62 to 64, and the arrangement confirmation sheet 72B is disposed at the vestibular side of the maxillary teeth 5 to 8, 65 to 67, and depending on whether the all indication lines 71 are overlapped with the confirm lines 74 or not, it can be determined whether the artificial teeth 1 to 8, 62 to 67 are arranged in normal state or not. If any deviation is found in the artificial teeth 1 to 8, 62 to 67, they can be adjusted to the specified position. Accordingly, advanced skills and experiences is not required for the operator for arranging teeth. Of course, these arrangement confirmation sheets 72A, 72B can be used not only after arrangement of all mandibular teeth 1 to 4, 62 to 64 and maxillary teeth 5 to 8, 65 to 67, but also during arrangement thereof.

The artificial teeth of the present invention are not limited to the configuration described in the embodiments, but may be changed in various forms.

For example, the configuration of the first embodiment of the arrangement direction indication parts including lateral grooves 17, 18, 25, 26, 41, 42, 49, 50, and the configuration of the second embodiment of the arrangement direction indication parts including arch expression part 68 may be combined with the configurations of third and fourth embodiments of arrangement direction indication parts of indication lines 71.

In particular, as shown in the first to third embodiments, the configuration of arrangement direction indication parts extended in the apical-cervical direction may be combined with the configuration of the fourth embodiment of arrangement direction indication parts extended in the mesiodistal direction, and the arrangement precision and the working efficiency may be substantially enhanced.

In the foregoing embodiments, the arrangement direction indication parts are provided on the vestibular side and/or oral side of the artificial teeth 1 to 8, 62 to 67, but in the case of molar teeth 1 to 8, in particular, the arrangement direction indication parts may be provided on the occlusal plane so as to be linear as seen from the occlusal plane. As a result, without requiring advanced skills and experiences, the arrangement position may be adjusted at high precision.

Further, as in the fourth embodiment, the configuration of forming the arrangement confirmation sheets 72A, 72B may be also combined with the configuration of the first to third embodiments, or with all embodiments, and may be similarly applicable. The arrangement confirmation sheets may not be divided for the mandibular teeth 1 to 4, 62 to 64 and the maxillary teeth 5 to 8, 65 to 67, but may be formed as one piece. In the foregoing embodiments, to cover all of each pair of mandibular teeth 1 to 4, 62 to 64 and maxillary teeth 5 to 8, 65 to 67, confirm lines 74 corresponding to all indication lines 71 are provided, but since they are symmetrical, and they may be formed only in half of them.

In the third and fourth embodiments, the indication lines 71 of the majority of the adjacent teeth are positioned nearly, but when arrangement confirmation sheets are used, in particular, only by disposing in parallel or in line, it is not required to form to be positioned linearly. What is more, the artificial teeth 1 to 8, 62 to 67 are provided in plural types slightly different in appearance depending on the shape of the remaining teeth of patient and the jaw shape, but when the arrangement confirmation sheets are used, all plural types may be formed to be identical in the position of the indication lines 71, and the arrangement confirmation sheets may be formed in one type only.

Although the present invention has been fully described by way of the examples with reference to the accompanying drawings, it is to be noted here that various changes and modifications will be apparent to those skilled in the art. Therefore, unless such changes and modifications otherwise depart from the spirit and scope of the present invention, they should be construed as being included therein.

What is claimed is:

1. A method of arranging a plurality of artificial teeth in a plate to be attached in an oral cavity as a dental prosthetic appliance, the method comprising:

positioning the artificial teeth in the plate, each artificial tooth of the artificial teeth comprising an arrangement direction indicator provided at a vestibular side surface or an oral side surface of the artificial tooth, the arrangement direction indicator showing a directivity of arrangement in the plate, the arrangement direction indicator comprising a line formed by coloring, wherein said line extends in a direction perpendicular or parallel to a mesiodistal direction when the artificial tooth is arranged in the plate;

placing an arrangement confirmation sheet on the vestibular or oral side surfaces of the artificial teeth mounted on the plate, the arrangement confirmation sheet comprising an elongated transparent and elastic sheet formed with line markings thereon; and adjusting the position of said each artificial tooth of the artificial teeth on the plate so as to match said arrangement direction indicator on said each artificial tooth with said line markings on the arrangement confirmation sheet.

2. The arranging method according to claim 1, wherein the arrangement direction indicator comprises two lines parallel to each other.

3. The arranging method according to claim 2, wherein, the lines of the arrangement direction indicators extend perpendicular to the mesiodistal direction when the artificial teeth are arranged in the plate.

4. The arranging method according to claim 2, wherein, the lines of the arrangement direction indicators extend parallel to the mesiodistal direction when the artificial teeth are arranged in the plate, the lines on the two adjacent teeth form a straight line.

* * * * *